(12) United States Patent
Caponigro et al.

(10) Patent No.: US 10,328,065 B2
(45) Date of Patent: *Jun. 25, 2019

(54) PHARMACEUTICAL COMBINATION COMPRISING THE PI3K INHIBITOR ALPELISIB AND THE B-RAF INHIBITOR DABRAFENIB; THE USE OF SUCH COMBINATION IN THE TREATMENT OR PREVENTION OF CANCER

(71) Applicant: Novartis AG, Basel (CH)

(72) Inventors: Giordano Caponigro, Foxborough, MA (US); Thomas Horn-Spirohn, Cambridge, MA (US); Joseph Lehar, Lexington, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/755,122

(22) PCT Filed: Aug. 24, 2016

(86) PCT No.: PCT/IB2016/055041
§ 371 (c)(1),
(2) Date: Feb. 26, 2018

(87) PCT Pub. No.: WO2017/037573
PCT Pub. Date: Mar. 9, 2017

(65) Prior Publication Data
US 2018/0243279 A1    Aug. 30, 2018

Related U.S. Application Data

(60) Provisional application No. 62/211,010, filed on Aug. 28, 2015.

(51) Int. Cl.
*A61P 35/02* (2006.01)
*A61K 31/506* (2006.01)
*A61K 31/4439* (2006.01)

(52) U.S. Cl.
CPC ........ *A61K 31/4439* (2013.01); *A61K 31/506* (2013.01); *A61P 35/02* (2018.01); *A61K 2300/00* (2013.01)

(58) Field of Classification Search
CPC .... A61P 35/02; A61K 31/506; A61K 31/4439
See application file for complete search history.

(56) References Cited

FOREIGN PATENT DOCUMENTS

| WO | 2014025688 | | 2/2014 |
|---|---|---|---|
| WO | WO 2015/022609 | * | 2/2015 |

OTHER PUBLICATIONS

Cancer Network Editors (Nov. 25, 2013).*
Menzies et al. (Clin. Cancer Res. 20(8) 1-9 2014).*
Deuker, M.M.et al., "PI3'-Kinase Inhibition Forestalls the Onset of MEK1/2 Inhibitor Resistance in BRAF-Mutated Melanoma", Cancer Discovery, vol. 5, No. 2, pp. 143-153, 2014.
Caponigro, Giordano et al., "Abstract 2337: Efficacy of the RAF/PI3K[alpha]/anti-EGFR Triple Combination LGX818 + BYL719 + Cetuximab in BRAFV600E Colorectal Tumor Models", Cancer Research, vol. 73, p. 2337, 2013.
Medina, T. et al., "Dabrafenib in the Treatment of Advanced Melanoma", Drugs of Today, vol. 49(6), pp. 377-385, 2013.
Mao, M. et al., "Resistance to BRAF Inhibition in BRAF-Mutant Colon Cancer can be Overcome with PI3K Inhibition on Demethylating Agents", Clinical Cancer Research, vol. 19(3), pp. 657-667, 2013.

* cited by examiner

*Primary Examiner* — Shirley V Gembeh
(74) *Attorney, Agent, or Firm* — Sandra Rueck

(57) ABSTRACT

The present disclosure relates to a pharmaceutical combination comprising (a) alpha-isoform specific PI3K inhibitor and (b) a B-RAF inhibitor; combined preparations and pharmaceutical compositions thereof; the uses of such combination in the treatment or prevention of cancer; and methods of treating or preventing cancer in a subject comprising administering a therapeutically effective amount of such combination.

3 Claims, 2 Drawing Sheets

PHARMACEUTICAL COMBINATION COMPRISING THE PI3K INHIBITOR ALPELISIB AND THE B-RAF INHIBITOR DABRAFENIB; THE USE OF SUCH COMBINATION IN THE TREATMENT OR PREVENTION OF CANCER

FIELD OF THE INVENTION

Provided herein is a pharmaceutical combination comprising (a) an alpha-isoform specific PI3K inhibitor and (b) a B-RAF inhibitor; pharmaceutical compositions comprising the same; and methods of using such combinations and compositions in the treatment or prevention of conditions in which the inhibition of an alpha-isoform specific PI3K inhibitor and a B-RAF inhibitor is beneficial, e.g., cancer.

BACKGROUND OF THE INVENTION

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., *Annu. Rev. Biochem.* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423(1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers.

Furthermore, mutations and translocation of p85α that serve to up-regulate the p85-p110 complex have been described in human cancers. Finally, somatic missense mutations in PIK3CA that activate downstream signaling pathways have been described at significant frequencies in a wide diversity of human cancers (Kang et al., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey et al., *Nature Rev. Drug Disc.* 4:988-1004 (2005)).

It has been found that the 2-carboxamide cycloamino urea derivatives of the Formula (I) given below have advantageous pharmacological properties and inhibit, for example, PI3K (phosphatidylinositol 3-kinase). In particular, these compounds preferably show an improved selectivity for PI3K alpha with respect to beta and/or, delta and/or gamma subtypes. Hence, the compounds of Formula (I) are suitable, for example, to be used in the treatment of diseases depending on PI3 kinases (in particular PI3K alpha, such as those showing overexpression or amplification of PI3K alpha or somatic mutation of PIK3CA), especially proliferative diseases such as tumor diseases and leukaemias.

Further, these compounds preferably show improved metabolic stability and hence reduced clearance, leading to improved pharmacokinetic profiles.

Mutations in various Ras GTPases and the B-RAF kinase have been identified that can lead to sustained and constitutive activation of the MAPK pathway, ultimately resulting in increased cell division and survival. As a consequence of this, these mutations have been strongly linked with the establishment, development, and progression of a wide range of human cancers. The biological role of the Raf kinases, and specifically that of B-RAF, in signal transduction is described in Davies, H., et al., *Nature* (2002) 9:1-6; Garnett, M. J. & Marais, R., *Cancer Cell* (2004) 6:313-319; Zebisch, A. & Troppmair, J., *Cell. Mol. Life Sci.* (2006) 63:1314-1330; Midgley, R. S. & Kerr, D. J., *Crit. Rev. Onc/Hematol.* (2002) 44:109-120; Smith, R. A., et al., *Curr. Top. Med. Chem.* (2006) 6:1071-1089; and Downward, J., *Nat. Rev. Cancer* (2003) 3:11-22.

Naturally occurring mutations of the B-RAF kinase that activate MAPK pathway signaling have been found in a large percentage of human melanomas (Davies (2002) supra) and thyroid cancers (Cohen et al *J. Nat. Cancer Inst.* (2003) 95(8) 625-627 and Kimura et al *Cancer Res.* (2003) 63(7) 1454-1457), as well as at lower, but still significant, frequencies in the following:

Barret's adenocarcinoma (Garnett et al., *Cancer Cell* (2004) 6 313-319 and Sommerer et al *Oncogene* (2004) 23(2) 554-558), billiary tract carcinomas (Zebisch et al., *Cell. Mol. Life Sci.* (2006) 63 1314-1330), breast cancer (Davies (2002) supra), cervical cancer (Moreno-Bueno et al *Clin. Cancer Res.* (2006) 12(12) 3865-3866), cholangiocarcinoma (Tannapfel et al *Gut* (2003) 52(5) 706-712), central nervous system tumors including primary CNS tumors such as glioblastomas, astrocytomas and ependymomas (Knobbe et al *Acta Neuropathol. (Berl.)* (2004) 108(6) 467-470, Davies (2002) supra, and Garnett et al., *Cancer Cell* (2004)

supra) and secondary CNS tumors (i.e., metastases to the central nervous system of tumors originating outside of the central nervous system), colorectal cancer, including large intestinal colon carcinoma (Yuen et al *Cancer Res.* (2002) 62(22) 6451-6455, Davies (2002) supra and Zebisch et al., *Cell. Mol. Life Sci.* (2006), gastric cancer (Lee et al *Oncogene* (2003) 22(44) 6942-6945), carcinoma of the head and neck including squamous cell carcinoma of the head and neck (Cohen et al *J. Nat. Cancer Inst.* (2003) 95(8) 625-627 and Weber et al *Oncogene* (2003) 22(30) 4757-4759), hematologic cancers including leukemias (Garnett et al., *Cancer Cell* (2004) supra, particularly acute lymphoblastic leukemia (Garnett et al., *Cancer Cell* (2004) supra and Gustafsson et al *Leukemia* (2005) 19(2) 310-312), acute myelogenous leukemia (AML) (Lee et al *Leukemia* (2004) 18(1) 170-172, and Christiansen et al *Leukemia* (2005) 19(12) 2232-2240), myelodysplastic syndromes (Christiansen et al *Leukemia* (2005) supra) and chronic myelogenous leukemia (Mizuchi et al *Biochem. Biophys. Res. Commun.* (2005) 326(3) 645-651); Hodgkin's lymphoma (Figl et al *Arch. Dermatol.* (2007) 143(4) 495-499), non-Hodgkin's lymphoma (Lee et al *Br. J. Cancer* (2003) 89(10) 1958-1960), megakaryoblastic leukemia (Eychene et al *Oncogene* (1995) 10(6) 1159-1165) and multiple myeloma (Ng et al *Br. J. Haematol.* (2003) 123(4) 637-645), hepatocellular carcinoma (Garnett et al., *Cancer Cell* (2004), lung cancer (Brose et al *Cancer Res.* (2002) 62(23) 6997-7000, Cohen et al *J. Nat. Cancer Inst.* (2003) supra and Davies (2002) supra), including small cell lung cancer (Pardo et al *EMBO J.* (2006) 25(13) 3078-3088) and non-small cell lung cancer (Davies (2002) supra), ovarian cancer (Russell & McCluggage *J. Pathol.* (2004) 203(2) 617-619 and Davies (2002) supr), endometrial cancer (Garnett et al., *Cancer Cell* (2004) supra, and Moreno-Bueno et al *Clin. Cancer Res.* (2006) supra), pancreatic cancer (Ishimura et al *Cancer Lett.* (2003) 199(2) 169-173), pituitary adenoma (De Martino et al *J. Endocrinol. Invest.* (2007) 30(1) RC1-3), prostate cancer (Cho et al *Int. J. Cancer* (2006) 119(8) 1858-1862), renal cancer (Nagy et al *Int. J. Cancer* (2003) 106(6) 980-981), sarcoma (Davies (2002) supra), and skin cancers (Rodriguez-Viciana et al *Science* (2006) 311(5765) 1287-1290 and Davies (2002) supra). Overexpression of c-Raf has been linked to AML (Zebisch et al., *Cancer Res.* (2006) 66(7) 3401-3408, and Zebisch (*Cell. Mol. Life Sci.* (2006)) and erythroleukemia (Zebisch et al., Cell. Mol. Life Sci. (2006).

By virtue of the role played by the Raf family kinases in these cancers and exploratory studies with a range of preclinical and therapeutic agents, including one selectively targeted to inhibition of B-RAF kinase activity (King A. J., et al., (2006) *Cancer Res.* 66:11100-11105), it is generally accepted that inhibitors of one or more Raf family kinases will be useful for the treatment of cancers associated with Raf kinase.

Many cancers, particularly those carrying B-RAF mutation, B-RAF V600E mutation, PIK3CA mutation and/or PIK3CA overexpression are amenable to treatments with, for example, a B-RAF inhibitor. However, in certain cases, the cancers acquire resistance to the chosen therapeutic and ultimately become refractory to treatment.

In spite of numerous treatment options for cancer patients, there remains a need for effective and safe therapeutic agents and a need for their preferential use in combination therapy. In particular, there is a need for effective methods of treating or preventing cancers, especially those cancers that have been resistant and/or refractory to current therapies.

SUMMARY OF THE INVENTION

Provided herein is a pharmaceutical combination comprising an alpha-isoform specific phosphatidylinositol 3-kinase (PI3K) inhibitor and a B-RAF inhibitor.

In one aspect, provided herein is a pharmaceutical combination comprising:

(a) a compound having the structure of Formula (I)

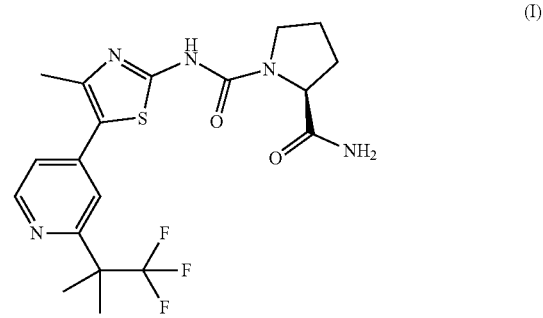 [SMILES: Cc1nc(NC(=O)N2CCC[C@H]2C(N)=O)sc1-c1ccnc(C(C)(C)C(F)(F)F)c1]

(also referred to herein as "Compound (I)" or "COMPOUND A")

or a pharmaceutically acceptable salt thereof, and (b) a compound having the structure of Formula (II)

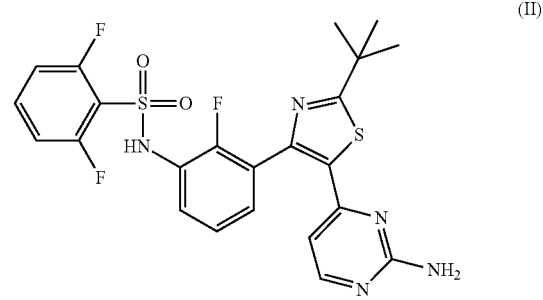 [SMILES: CC(C)(C)c1nc(-c2cccc(NS(=O)(=O)c3c(F)cccc3F)c2F)c(-c2ccnc(N)n2)s1]

(also referred to herein as "Compound (II)" or "COMPOUND B")

or a pharmaceutically acceptable salt thereof.

Combinations of the compound having the structure of Formula (I), or a pharmaceutically acceptable salt thereof, and a compound having the structure of Formula (II), or a pharmaceutically acceptable salt thereof will also be referred to herein as a "combination of the invention."

In an embodiment of the combination of the invention, the compound having the structure of Formula (I) or a pharmaceutically acceptable salt thereof and the compound having the structure of Formula (II) or a pharmaceutically acceptable salt thereof are in the same formulation. In another embodiment, the compound having the structure of Formula (I) or a pharmaceutically acceptable salt thereof and the compound having the structure of Formula (II) or a pharmaceutically acceptable salt thereof are in separate formulations.

In a further embodiment, the combination of the invention is for simultaneous or sequential administration.

In another aspect, provided herein is a method for treating or preventing cancer in a subject in need thereof comprising administering to the subject a therapeutically effective amount of the combination of the invention.

In an embodiment of the method, the cancer is a solid tumor.

In another embodiment, the cancer is selected from the group consisting of a benign or malignant tumor of the lung (including small cell lung cancer and non-small-cell lung cancer), bronchus, prostate, breast (including sporadic breast cancers and sufferers of Cowden disease), pancreas, gastrointestinal tract, colon, rectum, colon carcinoma, colorectal cancer, thyroid, liver, biliary tract, intrahepatic bile duct (including cholangiocarcinoma), hepatocellular, adrenal gland, stomach, gastric, glioma, CNS (including glioblastoma, astrocytomas, and ependymomas), endometrial, kidney, renal pelvis, bladder, uterus, cervix, vagina, ovary, multiple myeloma, esophagus, neck or head, brain, oral cavity and pharynx, larynx, small intestine, a melanoma, villous colon adenoma, a sarcoma, a neoplasia, a neoplasia of epithelial character, a mammary carcinoma, basal cell carcinoma, squamous cell carcinoma, actinic keratosis, polycythemia vera, essential thrombocythemia, a leukemia (including acute myelogenous leukemia, chronic myelogenous leukemia, acute lymphoblastic leukemia, chronic lymphoblastic leukemia, myelodysplastic syndromes, megakaryoblastic leukemia, erythroleukemia and myeloid leukemia), a lymphoma (including non-Hodgkin lymphoma and Hodgkin's lymphoma), myelofibrosis with myeloid metaplasia, Waldenstroem disease, and Barret's adenocarcinoma.

In another embodiment, the cancer is colorectal cancer or melanoma.

In another embodiment, the cancer is unresectable or metastatic melanoma.

In another embodiment, the cancer is characterized by one or more of a B-RAF mutation, B-RAF V600E mutation, PIK3CA mutation, and PIK3CA overexpression.

In another embodiment, the cancer is resistant or refractory to treatment with a B-RAF inhibitor.

In an embodiment, the combination of the invention is for use in the treatment or prevention of cancer.

In another embodiment, the combination of the invention is for use in the preparation of a medicament for the treatment or prevention of cancer.

In an aspect, provided herein is a use of the combination of the invention for the manufacture of a medicament for the treatment or prevention of cancer.

In another aspect, provided herein is a use of the combination of the invention for the treatment or prevention of cancer.

In an aspect, provided herein is a pharmaceutical composition comprising the combination of the invention.

In an embodiment, the pharmaceutical composition further comprises one or more excipients.

DETAILED DESCRIPTION OF THE INVENTION

Figure 1:
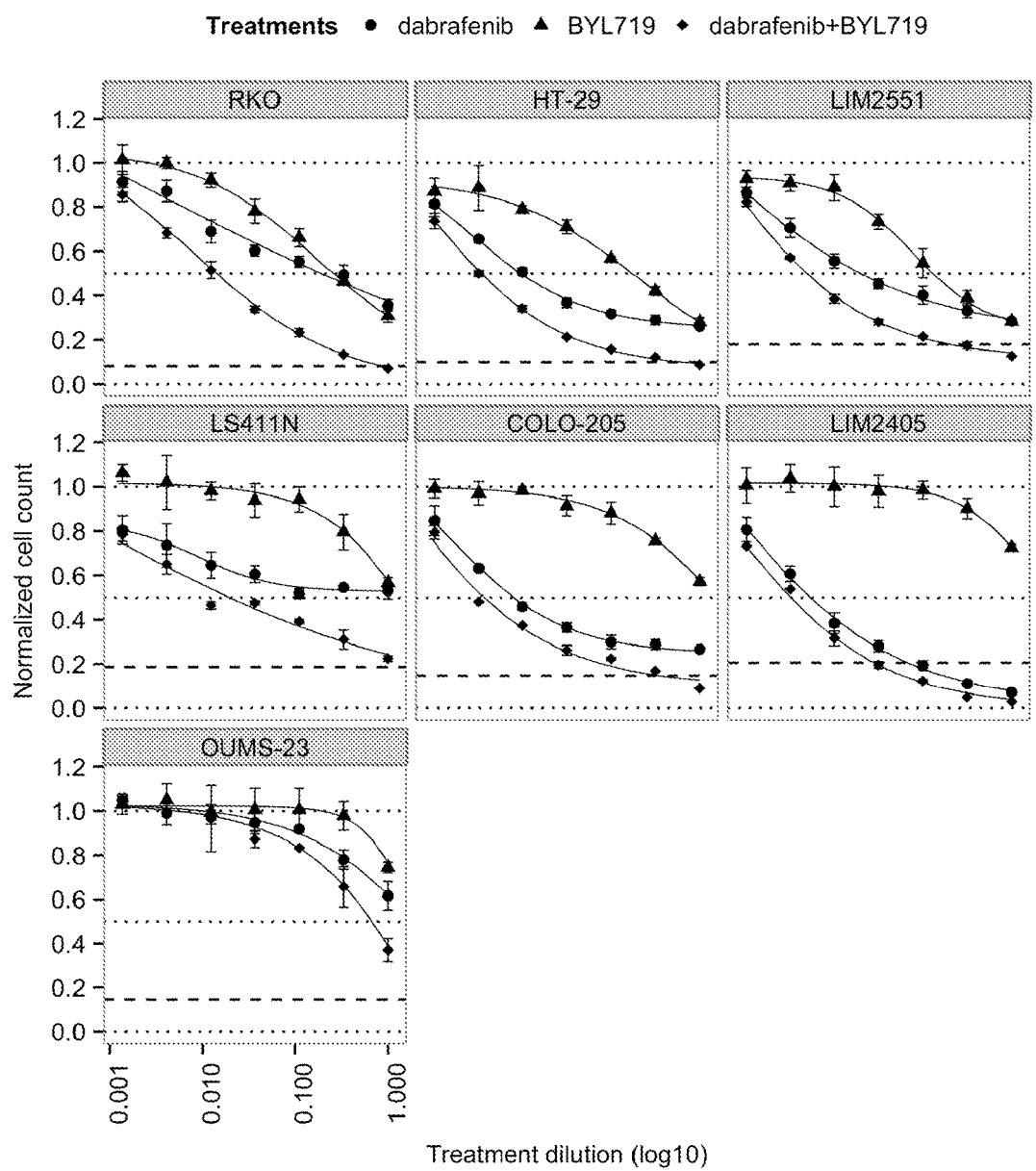
FIG. 1 shows dose-response curves for COMPOUND A (also referred to as BYL719) and COMPOUND B (also referred to as dabrafenib) and the combination of COMPOUND A and COMPOUND B over 7 BRAF mutant colorectal cancer cell lines. The x-axis indicates the log 10 of the treatment dilution; the y-axis indicates the cell count after treatment relative to DMSO. The strong dashed line indicates the number of cells before the start of the treatment ('baseline').

Provided herein is a pharmaceutical combination comprising an alpha-isoform specific phosphatidylinositol 3-kinase (PI3K) inhibitor and a B-RAF inhibitor. Specifically, provided herein is a pharmaceutical combination comprising:

(a) a compound having the structure of Formula (I)

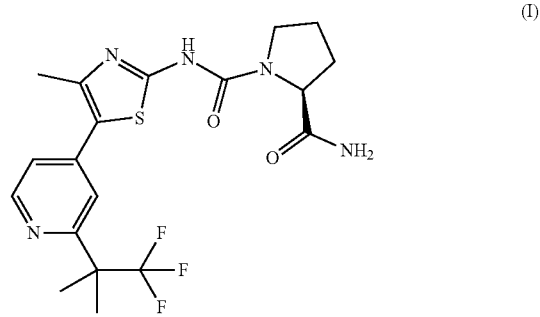 [SMILES: Cc1nc(NC(=O)N2CCC[C@H]2C(N)=O)sc1-c1ccnc(C(C)(C)C(F)(F)F)c1]

or a pharmaceutically acceptable salt thereof, and (b) a compound having the structure of Formula (II)

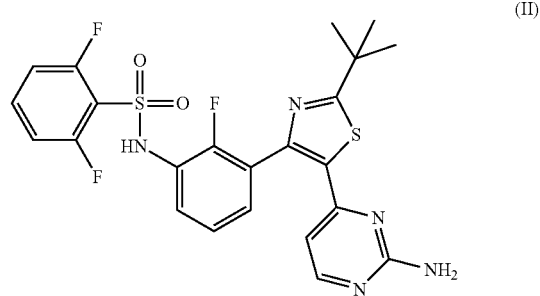 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof.

The pharmaceutical combination provided herein is, in particular, for use in the treatment or prevention of cancer.

Certain terms used herein are described below. Compounds of the present invention are described using standard nomenclature. Unless defined otherwise, all technical and scientific terms used herein have the same meaning as is commonly understood by one of skill in the art to which this invention belongs.

The term "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure.

Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

The terms "alpha-isoform specific phosphatidylinositol 3-kinase inhibitor," "alpha-isoform specific PI3K inhibitor," "alpha-isoform selective phosphatidylinositol 3-kinase inhibitor," and "alpha-isoform selective PI3K inhibitor" as used herein refer to a compound that selectively targets, decreases, or inhibits at least one activity of the alpha-isoform of PI3K with respect to beta and/or delta and/or gamma subtypes. Exemplary alpha-isoform specific PI3K inhibitors are disclosed in International PCT Application WO2010/029082, which is hereby incorporated by reference in its entirety.

The term "B-RAF inhibitor," as used herein refers to a compound that selectively targets, decreases or inhibits at least one activity of B-RAF.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" as used herein refers to those compounds, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

The terms "fixed combination," "fixed dose," and "single formulation" as used herein refers to a single carrier or vehicle or dosage form formulated to deliver an amount, which is jointly therapeutically effective for the treatment or prevention of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination," "kit of parts," and "separate formulations" means that the active ingredients, i.e., Compound (I) and Compound (II), are both administered to a patient as separate entities either simultaneously, concurrently or sequentially with no specific time limits, wherein such administration provides therapeutically effective levels of the two compounds in the body of the subject in need thereof. The latter also applies to cocktail therapy, e.g., the administration of three or more active ingredients.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, injections, infusions, patches, or the like, administered to the patient at the same time.

An "oral dosage form" includes a unit dosage form prescribed or intended for oral administration.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease. The term "protect" is used herein to mean prevent, delay, or treat, or all, as appropriate, development, continuance or aggravation of a disease in a subject, e.g., a mammal or human. The term "prevent", "preventing" or "prevention" as used herein comprises the prevention of at least one symptom associated with or caused by the state, disease or disorder being prevented.

The term "pharmaceutically effective amount," "therapeutically effective amount," or "clinically effective amount" of a combination of therapeutic agents is an amount sufficient to provide an observable or clinically significant improvement over the baseline clinically observable signs and symptoms of the disorders treated with the combination.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" or "approximately" are generally understood by persons knowledgeable in the relevant subject area, but in certain circumstances can mean within 20%, within 10%, or within 5% of a given value or range. Alternatively, especially in biological systems, the term "about" means within about a log (i.e., an order of magnitude) or within a factor of two of a given value.

As used herein, the PI3K inhibitor (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}- amide) (a compound having the structure of Formula (I), also referred to herein as "Compound (I)" or "COMPOUND A" or "BYL719") is a specific 2-carboxamide cycloamino urea derivative compound that potently and selectively targets the alpha (α)-isoform of class IA PI3K and has the following chemical structure:

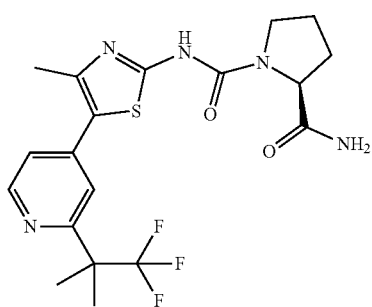

For convenience, the group of the compound and its salts is collectively referred to to as Compound (I), meaning that reference to Compound (I) will refer to any of the compound or pharmaceutically acceptable salt thereof in the alternative.

Compound (I) and its pharmaceutically acceptable salts are described in PCT Application No. WO2010/029082, which is hereby incorporated by reference in its entirety, and methods of its preparation have been described, for example, in Example 15 therein. The preparation of Compound (I) is also described herein in Example 1. Preferably, Compound (I) is in the free base form.

Compound (I) may be orally administered at an effective daily dose of about 1 to 6.5 mg/kg in human adults or children. Compound (I) may be orally administered to a 70 kg body weight human adult at a daily dosage of about 70 mg to 455 mg, e.g, about 200 to 400 mg, or about 240 mg to 400 mg, or about 300 mg to 400 mg, or about 350 mg to 400 mg, in a single dose or in divided doses up to four times a day. Preferably, Compound (I) is administered to a 70 kg body weight human adult at a daily dosage of about 350 mg to about 400 mg.

The salts of Compound (I) are preferably pharmaceutically acceptable salts; suitable counter-ions forming pharmaceutically acceptable salts are known in the field.

As used herein, the B-RAF inhibitor N-{3-[5-(2-Amino-4-pyrimidinyl)-2-(1,1-dimethylethyl)-1,3-thiazol-4-yl]-2-fluorophenyl}-2,6-difluorobenzenesulfonamide or pharmaceutically acceptable salt thereof, is a compound represented by the structure of Formula (II):

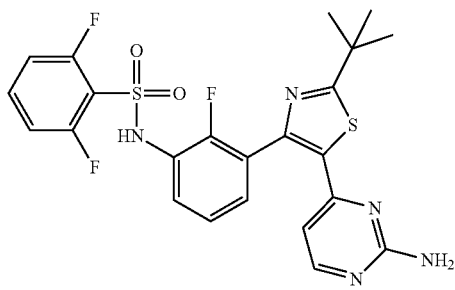

or a pharmaceutically acceptable salt thereof. Compound (II) is also known as dabrafenib. For convenience, the group of the compound and its salts is collectively referred to as Compound (II), meaning that reference to Compound (II) will refer to any of the compound or pharmaceutically acceptable salt thereof in the alternative.

Compound (II) is disclosed and claimed, along with pharmaceutically acceptable salts thereof, as being useful as an inhibitor of B-RAF activity, particularly in the treatment of cancer, in PCT patent application PCT/US09/42682, in which Compound (II) is embodied by Examples 58a through 58e. The PCT application was published on 12 Nov. 2009 as publication WO2009/137391, and is hereby incorporated by reference. Compound (II) may be prepared as described herein according to Example 2. Compound (II) may be administered orally.

Compound (II) (based on weight of the unsalted/unsolvated compound) may be administered as part of the combination at a daily dosage selected from about 10 mg to about 600 mg, e.g., about 30 mg to about 400 mg or about 100 mg to about 300 mg in human, in a single dose or in divided doses up to four times a day. Preferably, Compound (II) is administered to a 70 kg body weight human adult at a daily dosage of about 300 mg, e.g. 150 mg twice daily.

Compound (I) or Compound (II), or both, may be administered in free form or in pharmaceutically acceptable salt form. A "pharmaceutically acceptable salt", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. Preferably, Compound (II) is in the form of its mesylate salt.

Unless otherwise specified, or clearly indicated by the text, reference to therapeutic agents useful in the pharmaceutical combination provided herein includes both the free base of the compounds, and all pharmaceutically acceptable salts of the compounds.

Provided herein is a combination therapy comprising an alpha-isoform selective PI3K inhibitor Compound (I), or a pharmaceutically acceptable salt thereof, and a B-RAF inhibitor Compound (II), or a pharmaceutically acceptable salt thereof. Administration of the combination includes administration of the combination in a single formulation or unit dosage form, administration of the individual agents of the combination concurrently but separately, or administration of the individual agents of the combination sequentially by any suitable route. The dosage of the individual agents of the combination can require more frequent administration of one of the agent(s) as compared to the other agent(s) in the combination. Therefore, to permit appropriate dosing, packaged pharmaceutical products can contain one or more dosage forms that contain the combination of agents, and one or more dosage forms that contain one of the combination of agents, but not the other agent(s) of the combination.

The present invention particularly pertains to a combination of the invention for treating or preventing cancer. In an embodiment, the combination of the invention is used for the treatment or prevention of cancer comprising administering to the subject a combination therapy, comprising an effective amount of a compound having the structure of Formula (I) or a pharmaceutically acceptable salt thereof, and an effective amount of the compound having the structure of Formula (II), or a pharmaceutically acceptable salt thereof. Preferably, these compounds are administered at therapeutically effective dosages which, when combined, provide a beneficial effect. The administration may be separate, simultaneous, or sequential.

Thus, in an embodiment, the combination of the invention is for use in the treatment or prevention of cancer. In an embodiment, the combination is for use in the treatment of cancer.

Also provided herein is a use of the combination of the invention for the treatment or prevention of cancer. In an embodiment, the use of the combination is for the treatment of cancer.

In an embodiment, the cancer is a solid tumor. The term "solid tumor" especially means melanoma, breast cancer, ovarian cancer, colorectal cancer, and generally gastrointestinal tract, cervix cancer, lung cancer (including small-cell lung cancer and non-small cell lung cancer), head and neck cancer, bladder cancer, or prostate cancer. The present combination inhibits the growth of solid tumors and also liquid tumors. Further, depending on the tumor type and particular combination used, a decrease of the tumor volume can be obtained. The combination of the invention disclosed herein is also suited to prevent the metastatic spread of tumors and the growth or development of micrometastases. The combination disclosed herein is suitable for the treatment of poor prognosis patients, and is especially suitable for such poor prognosis patients as those having metastatic melanoma or colorectal cancer.

In another embodiment of any of the pharmaceutical combination provided herein, the cancer is selected from a benign or malignant tumor of the lung (including small cell lung cancer and non-small-cell lung cancer), bronchus, prostate, breast (including sporadic breast cancers and sufferers of Cowden disease), pancreas, gastrointestinal tract, colon, rectum, colon carcinoma, colorectal cancer, thyroid, liver, biliary tract, intrahepatic bile duct (including cholangiocarcinoma), hepatocellular, adrenal gland, stomach, gastric, glioma, CNS (including glioblastoma, astrocytomas, and ependymomas), endometrial, kidney, renal pelvis, bladder, uterus, cervix, vagina, ovary, multiple myeloma, esophagus, neck or head, brain, oral cavity and pharynx, larynx, small intestine, a melanoma, villous colon adenoma, a sarcoma, a neoplasia, a neoplasia of epithelial character, a mammary carcinoma, basal cell carcinoma, squamous cell carcinoma, actinic keratosis, polycythemia vera, essential thrombocythemia, a leukemia (including acute myelogenous leukemia, chronic myelogenous leukemia, acute lymphoblastic leukemia, chronic lymphoblastic leukemia, myelodysplastic syndromes, megakaryoblastic leukemia, erythroleukemia and myeloid leukemia), a lymphoma (including non-Hodgkin lymphoma and Hodgkin's lymphoma), myelofibrosis with myeloid metaplasia, Waldenstroem disease, and Barret's adenocarcinoma.

In another embodiment, the cancer is colorectal cancer or melanoma.

In another embodiment, the cancer is unresectable or metastatic melanoma.

In another embodiment, the cancer is characterized by one or more of B-RAF mutation, B-RAF V600E mutation, PIK3CA mutation, and PIK3CA overexpression.

In another embodiment, the cancer is resistant or refractory to treatment with a B-RAF inhibitor.

The nature of cancer is multifactorial. Under certain circumstances, drugs with different mechanisms of action may be combined. However, just considering any combination of therapeutic agents having different mode of action does not necessarily lead to combinations with advantageous effects.

The administration of a pharmaceutical combination of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the pharmaceutically therapeutic agents used in the combination of the invention.

A further benefit is that lower doses of the therapeutic agents of the combination of the invention can be used, for example, such that the dosages may not only often be smaller, but also may be applied less frequently, or can be used in order to diminish the incidence of side-effects observed with one of the combination partners alone. This is in accordance with the desires and requirements of the patients to be treated.

It can be shown by established test models that a combination of the invention results in the beneficial effects described herein before. The person skilled in the art is fully enabled to select a relevant test model to prove such beneficial effects. The pharmacological activity of a combination of the invention may, for example, be demonstrated in a clinical study or in an animal model.

In determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in certain experiments (see, e.g., Example 3) can be predictive of the effect in other species, and animal models exist may be used to further quantify a synergistic effect. The results of such studies can also be used to predict effective dose ratio ranges and the absolute doses and plasma concentrations.

In an embodiment, the combination or composition, or both, provided herein display a synergistic effect. The term "synergistic effect" as used herein, refers to action of two agents such as, for example, Compound (I) or a pharmaceutically acceptable salt thereof, and Compound (II), to produce an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. An additional method to show the synergistic effect is the highest single agent model (HSA) as null hypothesis (Berenbaum 1989). Excess over the HSA model predicts a functional connection between the inhibited targets (Lehar, Zimmermann et al. 2007, Lehar, Krueger et al. 2009). This method results in an indicator for the strength of the combination, $z_c$ (see, e.g., Example 3, including Table 2 for the $z_c$ scores of certain embodiments of the combination of the invention).

In a further embodiment, the present invention provides a synergistic combination for administration to humans comprising the combination of the invention, where the dose range of each component corresponds to the synergistic ranges suggested in a suitable tumor model or clinical study.

In another aspect, provided herein is a pharmaceutical composition such as a combined preparation or a pharmaceutical composition which comprises (a) Compound (I), or a pharmaceutically acceptable salt thereof, and (b) Compound (II), or a pharmaceutically acceptable salt thereof. In an embodiment, the pharmaceutical composition further comprises one or more excipients. In a further embodiment, the pharmaceutical composition further comprises one or more pharmaceutically acceptable excipients.

As used herein, the term "pharmaceutically acceptable excipient" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

In this composition, the combination partners can be administered in a single formulation or unit dosage form, administered concurrently but separately, or administered sequentially by any suitable route. The unit dosage form may also be a fixed combination.

The pharmaceutical compositions for separate administration of the combination partners, or for the administration in a fixed combination, i.e., a single galenical composition comprising the combination of the invention, may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g., as indicated above, or in combination with one or more pharmaceutically acceptable carriers, especially suitable for enteral or parenteral application.

The pharmaceutical composition may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, melt granulation, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

In an aspect, provide herein is a use of the combination of the invention for the manufacture of a medicament for the treatment or prevention of cancer. In an embodiment, the use of the pharmaceutical combination is for the manufacture of a medicament for the treatment of cancer.

In another aspect, provided herein is the combination of the invention for use in the preparation of a medicament for the treatment or prevention of cancer. In an embodiment, the combination is for use in the preparation of a medicament for the treatment of cancer.

A therapeutically effective amount of each of the combination partner of the combination of the invention may be administered simultaneously or sequentially and in any order, and the components may be administered as the same formulation, or as separate formulations.

The effective dosage of each of the combination partners employed in the combination of the invention may vary depending on the particular compound or pharmaceutical composition employed, the mode of administration, the condition being treated, and the severity of the condition being treated. Thus, the dosage regimen of the combination of the invention is selected in accordance with a variety of factors including the route of administration and the renal and hepatic function of the patient.

The optimum ratios, individual and combined dosages, and concentrations of the combination partners (e.g., Compound (I) and Compound (II)) of the combination of the invention that yield efficacy without toxicity are based on the kinetics of the therapeutic agents' availability to target sites, and are determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the combination partners, which are employed in the combination of the invention, are applied in the form as marketed as single drugs, their dosage and mode of administration can be in accordance with the information provided on the package insert of the respective marketed drug, if not mentioned herein otherwise.

The optimal dosage of each combination partner for treatment or prevention of a cancer can be determined empirically for each individual using known methods and will depend upon a variety of factors, including, though not limited to: the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone. Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art.

The present invention further provides a commercial package comprising, as therapeutic agents, the combination of the invention, together with instructions for simultaneous, separate or sequential administration thereof for use in the delay of progression or treatment of a cancer.

Methods for Treating

Provided herein is a method for treating or preventing cancer in a subject in need thereof comprising administering to the subject a therapeutically effective amount of a pharmaceutical combination of the invention, i.e., a pharmaceutical combination comprising:

(a) a compound having the structure of Formula (I)

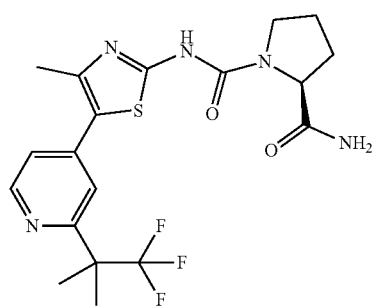

(I)

or a pharmaceutically acceptable salt thereof, and
(b) a compound having the structure of Formula (II)

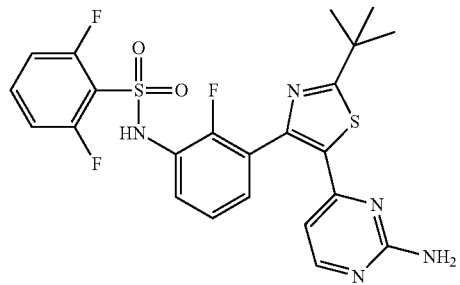

(II)

or a pharmaceutically acceptable salt thereof.

In an embodiment, provided herein is a method for treating or preventing cancer in a subject in need thereof comprising administering to the subject a therapeutically effective amount of a combination of the invention. In a further embodiment, provided herein is a method for treating cancer in a subject in need thereof comprising administering to the subject a therapeutically effective amount of a combination of the invention.

In an embodiment of any of the methods of the invention, the cancer is a solid tumor. The present methods can inhibit the growth of solid tumors and also liquid tumors. Further, depending on the tumor type and particular combination used, a decrease of the tumor volume can be obtained. The method disclosed herein is also suited to prevent the metastatic spread of tumors and the growth or development of micrometastases. The method disclosed herein is suitable for the treatment of poor prognosis patients, especially such poor prognosis patients having metastatic melanoma or colorectal cancer.

In another embodiment of any of the methods provided herein, the cancer is selected from a benign or malignant tumor of the lung (including small cell lung cancer and non-small-cell lung cancer), bronchus, prostate, breast (including sporadic breast cancers and sufferers of Cowden disease), pancreas, gastrointestinal tract, colon, rectum, colon carcinoma, colorectal cancer, thyroid, liver, biliary tract, intrahepatic bile duct (including cholangiocarcinoma), hepatocellular, adrenal gland, stomach, gastric, glioma, CNS (including glioblastoma, astrocytomas, and ependymomas), endometrial, kidney, renal pelvis, bladder, uterus, cervix, vagina, ovary, multiple myeloma, esophagus, neck or head, brain, oral cavity and pharynx, larynx, small intestine, a melanoma, villous colon adenoma, a sarcoma, a neoplasia, a neoplasia of epithelial character, a mammary carcinoma, basal cell carcinoma, squamous cell carcinoma, actinic keratosis, polycythemia vera, essential thrombocythemia, a leukemia (including acute myelogenous leukemia, chronic myelogenous leukemia, acute lymphoblastic leukemia, chronic lymphoblastic leukemia, myelodysplastic syndromes, megakaryoblastic leukemia, erythroleukemia and myeloid leukemia), a lymphoma (including non-Hodgkin lymphoma and Hodgkin's lymphoma), myelofibrosis with myeloid metaplasia, Waldenstroem disease, and Barret's adenocarcinoma.

In another embodiment, the cancer is colorectal cancer or melanoma.

In another embodiment, the cancer is unresectable or metastatic melanoma.

In another embodiment, the cancer is characterized by one or more of a B-RAF mutation, B-RAF V600E mutation, PIK3CA mutation, and PIK3CA overexpression.

In another embodiment cancer is resistant or refractory to treatment with a B-RAF inhibitor.

The method of treating or preventing cancer according to the invention may comprise (i) administration of the agent (a) in free or pharmaceutically acceptable salt form and (ii) administration of agent (b) in free or pharmaceutically acceptable salt form simultaneously or sequentially in any order, in jointly therapeutically effective amounts, preferably in synergistically effective amounts, e.g., in daily or intermittent dosages corresponding to the amounts described herein. The individual combination partners of the combination of the invention may be administered separately at different times during the course of therapy or concurrently in divided or single combination forms. The invention is therefore to be understood as embracing all such regimens of simultaneous or alternating treatment and the term "administering" is to be interpreted accordingly.

The following Examples illustrate the invention described above; they are not, however, intended to limit the scope of the invention in any way. The beneficial effects of the pharmaceutical combination of the present invention can also be determined by other test models known as such to the person skilled in the pertinent art.

EXAMPLES

Example 1

I. Synthesis of (S)-Pyrrolidine-1,2-dicarboxylic acid 2-amide 1-{[5-(2-tert-butyl-pyridin-4-yl)-4-methyl-thiazol-2-yl]-amide}

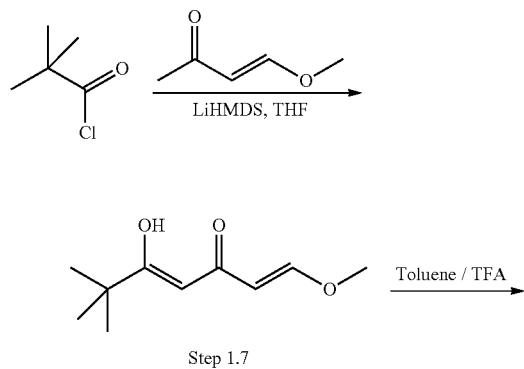

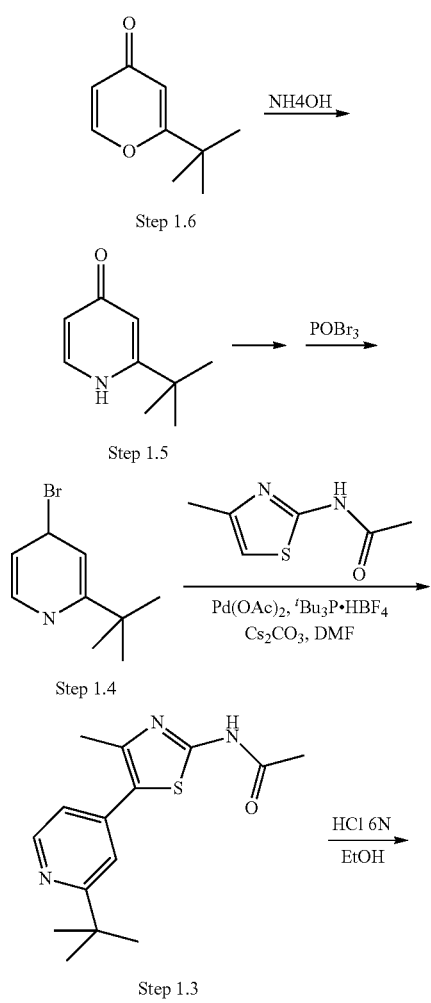

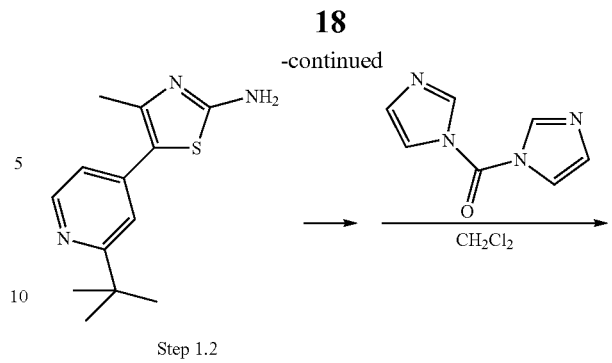

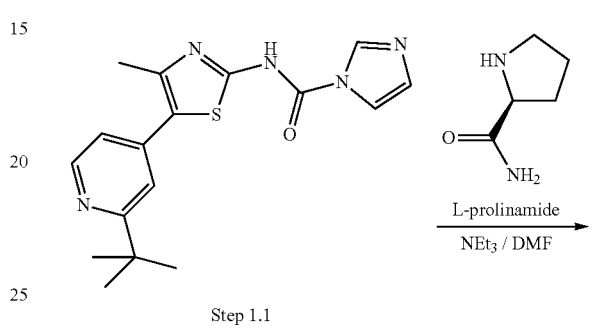

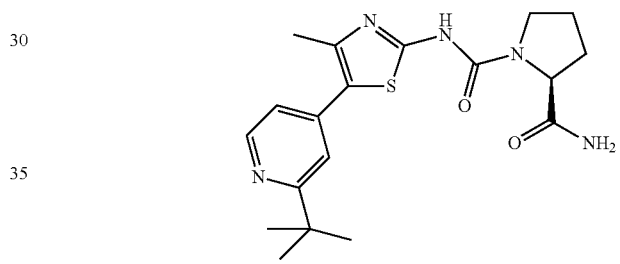

Example 1

Et$_3$N (1.54 mL, 11.1 mmol, 3 eq) is added to a solution of imidazole-1-carboxylic acid [5-(2-tert-butyl-pyridin-4-yl)-4-methyl-thiazol-2-yl]-amide (Step 1.1) (1.26 g, 3.7 mmol) and L-prolinamide (0.548 g, 4.8 mmol, 1.3 eq) in DMF (25 mL), under an argon atmosphere. The reaction mixture is stirred for 14 h at rt, quenched by addition of a saturated solution of NaHCO$_3$, and extracted with EtOAc. The organic phase is washed with a saturated solution of NaHCO$_3$, dried (Na$_2$SO$_4$), filtered and concentrated. The residue is purified by silica gel column chromatography (DCM/MeOH, 1:0→94:6), followed by trituration in Et$_2$O to afford 1.22 g of the title compound as an off-white solid: ESI-MS: 388.1 [M+H]$^+$; t$_R$=2.35 min (System 1); TLC: R$_f$=0.36 (DCM/MeOH, 9:1). $^1$H NMR (400 MHz, DMSO-d6) δ(ppm): 1.32 (s, 9H) 1.75-1.95 (m, 3H) 1.97-2.13 (m, 1H) 2.39 (s, 3H) 3.38-3.50 (m, 1H) 3.52-3.65 (m., 1H) 4.10-4.40 (m, 1H) 6.94 (br. s., 1H) 7.22 (d, 1H) 7.30-7.48 (m, 2H) 8.49 (d, 1H) 10.87 (br. s., 1H).

Step 1.1: Imidazole-1-carboxylic acid [5-(2-tert-butyl-pyridin-4-yl)-4-methyl-thiazol-2-yl]-amide

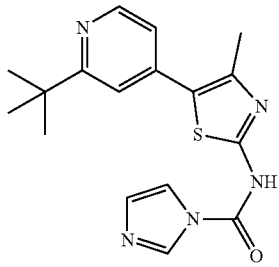 [SMILES: Cc1nc(NC(=O)n2ccnc2)sc1-c1ccnc(C(C)(C)C)c1]

A mixture of 5-(2-tert-butyl-pyridin-4-yl)-4-methyl-thiazol-2-ylamine (Step 1.2) (1 g, 4.05 mmol) and 1,1'-carbonyldiimidazole (0.984 g, 6.07 mmol, 1.5 eq) in DCM (50 mL) is stirred for 4 h at reflux and allowed to cool. The resulting precipitate is collected by filtration to provide 1.26 g of the title compound as white solid: ESI-MS: 340.2 [M−H]$^-$; $t_R$=2.85 min (System 1).

Step 1.2: 5-(2-tert-Butyl-pyridin-4-yl)-4-methyl-thiazol-2-ylamine

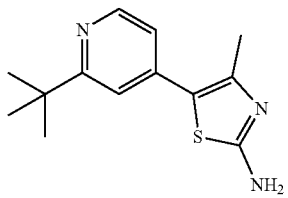 [SMILES: Cc1nc(N)sc1-c1ccnc(C(C)(C)C)c1]

A mixture of N-[5-(2-tert-butyl-pyridin-4-yl)-4-methyl-thiazol-2-yl]-acetamide (Step 1.3) (2 g, 7 mmol), a 6N aqueous solution of HCl (10 mL) and EtOH (50 mL) is stirred for 2 h at 85° C., allowed to cool, quenched by addition of a saturated solution of NaHCO$_3$ and extracted with DCM/MeOH (9:1, v/v). The organic phase is washed with a saturated solution of NaHCO$_3$, dried (Na$_2$SO$_4$), filtered and concentrated. The residue is purified by silica gel column chromatography (DCM/MeOH, 1:0→96:4) to afford 1.21 g of the title compound as a yellow solid: ESI-MS: 248.1 [M+H]$^+$; TLC: $R_f$=0.36 (DCM/MeOH, 9:1).

Step 1.3: N-[5-(2-tert-Butyl-pyridin-4-yl)-4-methyl-thiazol-2-yl]-acetamide

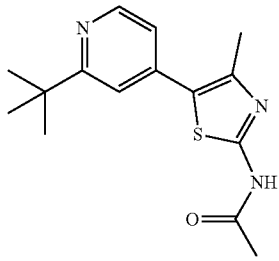 [SMILES: CC(=O)Nc1nc(C)c(-c2ccnc(C(C)(C)C)c2)s1]

A mixture of 2-acetamido-4-methylthiazole (1.2 g, 7.7 mmol, 1.1 eq), cesium carbonate (4.55 g, 14 mmol, 2 eq), tri-tert-butylphosphinium tetrafluoroborate (0.406 g, 1.4 mmol, 0.2 eq), palladium (II) acetate (0.15 g, 0.7 mmol, 0.1 eq) and 4-bromo-2-tert-butyl-pyridine (Step 1.4) (1.5 g, 7 mmol) in DMF (50 mL) is stirred for 1.5 h at 90° C. under an argon atmosphere, allowed to cool, quenched by addition of a saturated solution of NaHCO$_3$ and filtered through a pad of celite. The filtrate is extracted with EtOAc. The organic phase is washed with a saturated solution of NaHCO$_3$, dried (Na$_2$SO$_4$), filtered and concentrated. The residue is purified by silica gel column chromatography (DCM/MeOH, 1:0→97:3) to afford 2.02 g of the title compound as a yellow solid: ESI-MS: 290.1 [M+H]$^-$; TLC: $R_f$=0.35 (DCM/MeOH, 9:1).

Step 1.4: 4-Bromo-2-tert-butyl-pyridine

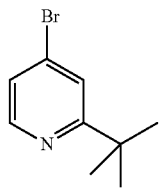

A mixture of 2-tert-butyl-1H-pyridin-4-one (Step 1.5) (4.25 g, 28 mmol) and POBr$_3$ (8.88 g, 31 mmol, 1.1 eq) is heated to 120° C., stirred for 15 min, allowed to cool, quenched by addition of a saturated solution of NaHCO$_3$ and extracted with DCM/MeOH (9:1, v/v). The organic phase is washed with a saturated solution of NaHCO$_3$, dried (Na$_2$SO$_4$), filtered and concentrated. The residue is purified by silica gel column chromatography (Hex/EtOAc, 95:5) to afford 5.18 g of the title compound as a yellow oil: ESI-MS: 214.0/216.0 [M+H]$^+$; $t_R$=2.49 min (System 1); TLC: $R_f$=0.35 (Hex/EtOAc, 1:1).

Step 1.5: 2-tert-Butyl-1H-pyridin-4-one

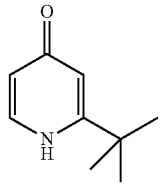

A mixture of 2-tert-butyl-pyran-4-one (Step 1.6) (5.74 g, 37.7 mmol) and a 30% aqueous solution of ammonium hydroxide (100 mL) is stirred for 1 h at reflux, allowed to cool and concentrated. The residue is triturated with MeOH (200 mL) and filtered. The filtrate is concentrated and the residue purified by silica gel column chromatography (DCM/MeOH/NH$_{3aq}$, 94:5:1→92:7:1) to afford 4.46 g of the title compound as a yellow solid: ESI-MS: 152.0 [M+H]$^-$; $t_R$=1.45 min (System 1); TLC: $R_f$=0.11 (DCM/MeOH, 9:1).

Step 1.6: 2-tert-Butyl-pyran-4-one

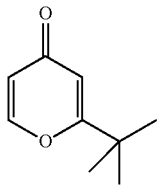

A mixture of 5-hydroxy-1-methoxy-6,6-dimethyl-hepta-1,4-dien-3-one (Step 1.7) (6.8 g, 36.9 mmol) and TFA (5.65 mL, 74 mmol, 2 eq) in benzene (250 mL) is stirred for 14 h at rt and concentrated. Purification of the residue by silica gel column chromatography (Hex/EtOAc, 1:0→75:25) provides 5.74 g of the title compound as a yellow oil: ESI-MS: 153.1 $[M+H]^+$; $t_R$=3.21 min (System 1); TLC: $R_f$=0.22 (Hex/EtOAc, 1:1).

Step 1.7: 5-Hydroxy-1-methoxy-6,6-dimethyl-hepta-1,4-dien-3-one

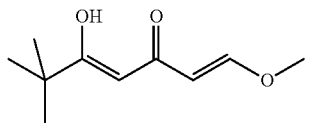

LiHMDS (1M in THF, 100 mL, 2 eq) is added dropwise to a cold (−78° C.) solution of 4-methoxy-3-buten-2-one (10 mL, 100 mmol, 2 eq) in THF (400 mL). After a 30 min stirring at −78° C., a solution of pivaloyl chloride (6.12 mL, 50 mmol) in THF (100 mL) is added. The resulting mixture is allowed to warm to rt over 2 h and quenched by addition of a saturated solution of $NH_4Cl$. THF is removed under vacuum. The concentrated mixture is extracted with $Et_2O$. The organic phase is washed with brine, dried ($Na_2SO_4$), filtered and concentrated. The residue is purified by silica gel column chromatography (Hex/EtOAc, 1:0→85:15) to afford 6.83 g of the title compound as a yellow oil: ESI-MS: 185.1 $[M+H]^+$; TLC: $R_f$=0.87 (Hex/EtOAc, 1:1).

II. Synthesis of (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (Compound (I) or COMPOUND A or BYL719)

The title compound is prepared in analogy to the procedure described in above, but with the following modifications. In Step 1.1, the reaction mixture is stirred for 14 h at reflux. In Step 1.2, the reaction mixture is stirred for 1 h at 85° C. and extracted with EtOAc after being quenched. In Step 1.3, the reaction mixture is stirred for 2.5 h at 120° C. In Step 1.4, the reaction mixture is stirred for 1 h at 83° C. and extracted with EtOAc after being quenched. In Step 1.5, the reaction mixture is stirred for 1 h at 65° C. and trituration in MeOH is not performed. In Step 1.6, the crude product is not purified. In Step 1.7, 3,3,3-trifluoro-2,2-dimethyl-propionyl chloride is used.

Title compound: ESI-MS: 442.0 $[M+H]^+$; $t_R$=3.02 min (System 1); TLC: $R_f$=0.35 (DCM/MeOH, 9:1). $^1$H NMR (400 MHz, DMSO-d6) δ(ppm): 1.60 (s, 6H) 1.70-1.95 (m, 3H) 1.99-2.16 (m, 1H) 2.40 (s, 3H) 3.38-3.51 (m, 1H) 3.51-3.69 (m, 1H) 4.10-4.40 (m, 1H) 6.95 (br. s., 1H) 7.39 (d, 2H) 7.53 (s, 1H) 8.58 (d, 1H) 10.93 (br. s., 1H)

In an alternative procedure the title compound is prepared in analogy to the procedure described above, but with the following modifications: N,N-Dimethylacetamide is used instead of DMF and the mixture is stirred at 65° C. for 2 h. In Step 1.1, phenyl chloroformate (added slowly) is used instead of 1,1'-carbonyldiimidazole and the reaction is carried out in THF in the presence of N,N-diethyl-isopropylamine at room temperature (1.5 h). In Step 1.2, the reaction mixture is heated under stirring for 5 h under (reflux) and extracted with EtOAc after being quenched. In Step 1.3, the reaction mixture is stirred for 2 h at 100° C. In Step 1.4, the reaction is run in toluene using 1.1 equivalents of $POBr_3$ and 1.1 equivalents of tripropylamine and the mixture is stirred for 2 h at 80° C. and extracted with EtOAc after being quenched. In Step 1.5, the reaction mixture is stirred for 1 h at 65° C. and trituration in MeOH is not performed. In Step 1.6, toluene is used instead of benzene and the crude product is not purified. In Step 1.7, 3,3,3-trifluoro-2,2-dimethyl-propionyl chloride is used.

Example 2: Synthesis of Compound (II) (COMPOUND B)

Method 1: Compound B (first crystal form)—N-{3-[5-(2-Amino-4-pyrimidinyl)-2-(1,1-dimethylethyl)-1,3-thiazol-4-yl]-2-fluorophenyl}-2,6-difluorobenzenesulfonamide

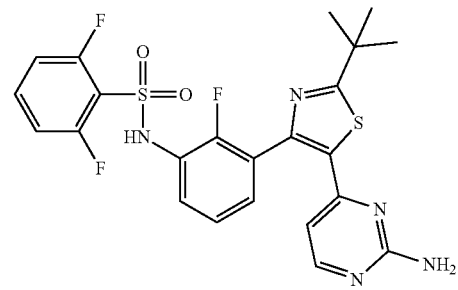

(II)

A suspension of N-{3-[5-(2-chloro-4-pyrimidinyl)-2-(1,1-dimethylethyl)-1,3-thiazol-4-yl]-2-fluorophenyl}-2,6-difluorobenzenesulfonamide (196 mg, 0.364 mmol) and ammonia in methanol 7M (8 ml, 56.0 mmol) was heated in a sealed tube to 90° C. for 24 h. The reaction was diluted with DCM and added silica gel and concentrated. The crude product was chromatographed on silica gel eluting with 100% DCM to 1:1 [DCM:(9:1 EtOAc:MeOH)]. The clean fractions were concentrated to yield the crude product. The crude product was repurified by reverse phase HPLC (a gradient of acetonitrile:water with 0.1% TFA in both). The combined clean fractions were concentrated then partitioned between DCM and saturated $NaHCO_3$. The DCM layer was separated and dried over $Na_2SO_4$. The title compound, N-{3-[5-(2-amino-4-pyrimidinyl)-2-(1,1-dimethylethyl)-1,3-thiazol-4-yl]-2-fluorophenyl}-2,6-difluorobenzenesulfonamide was obtained (94 mg, 47% yield). $^1$H NMR (400 MHz, DMSO-d6) δ ppm 10.83 (s, 1H), 7.93 (d, J=5.2 Hz, 1H), 7.55-7.70 (m, 1H), 7.35-7.43 (m, 1H), 7.31 (t, J=6.3 Hz, 1H), 7.14-7.27 (m, 3H), 6.70 (s, 2H), 5.79 (d, J=5.13 Hz, 1H), 1.35 (s, 9H). MS (ESI): 519.9 $[M+H]^+$.

Method 2: Compound B (alternative crystal form)—N-{3-[5-(2-Amino-4-pyrimidinyl)-2-(1,1-dimethylethyl)-1,3-thiazol-4-yl]-2-fluorophenyl}-2,6-difluorobenzenesulfonamide 19.6 mg of N-{3-[5-(2-Amino-4-pyrimidinyl)-2-(1,1-dimethylethyl)-1,3-thiazol-4-yl]-2-fluorophenyl}-2,6-difluorobenzenesulfonamide (may be prepared in accordance with example 58a of PCT/US09/42682) was combined with 500 μL of ethyl acetate in a 2-mL vial at room temperature. The slurry was temperature-cycled between 0-40° C. for 48 hrs. The resulting slurry was allowed to cool to room temperature and the solids were collected by vacuum filtration. The solids were analyzed by Raman, PXRD, DSC/TGA analyses, which indicated a crystal form different from the crystal form resulting from Example 58a (of PCT/US09/42682).

Method 3: Compound B (alternative crystal form, large batch)—N-{3-[5-(2-amino-4-pyrimidinyl)-2-(1,1-dimethylethyl)-1,3-thiazol-4-yl]-2-fluorophenyl}-2,6-difluorobenzenesulfonamide

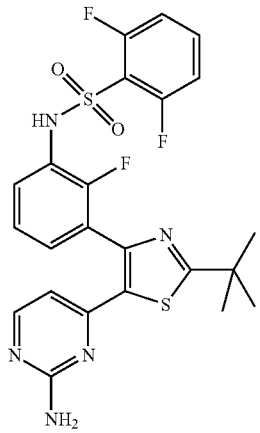 [SMILES: CC(C)(C)c1nc(-c2cccc(NS(=O)(=O)c3c(F)cccc3F)c2F)c(-c2ccnc(N)n2)s1]

Step A: methyl 3-{[(2,6-difluorophenyl)sulfonyl]amino}-2-fluorobenzoate

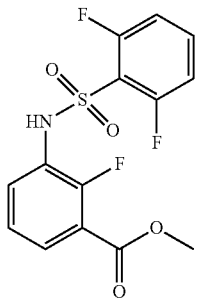 [SMILES: COC(=O)c1cccc(NS(=O)(=O)c2c(F)cccc2F)c1F]

Methyl 3-amino-2-fluorobenzoate (50 g, 1 eq) was charged to reactor followed by dichloromethane (250 mL, 5 vol). The contents were stirred and cooled to ~15° C. and pyridine (26.2 mL, 1.1 eq) was added. After addition of the pyridine, the reactor contents were adjusted to ~15° C. and the addition of 2,6-diflurorobenzenesulfonyl chloride (39.7 mL, 1.0 eq) was started via addition funnel. The temperature during addition was kept <25° C. After complete addition, the reactor contents were warmed to 20-25° C. and held overnight. Ethyl acetate (150 mL) was added and dichloromethane was removed by distillation. Once distillation was complete, the reaction mixture was then diluted once more with ethyl acetate (5 vol) and concentrated. The reaction mixture was diluted with ethyl acetate (10 vol) and water (4 vol) and the contents heated to 50-55° C. with stirring until all solids dissolve. The layers were settled and separated. The organic layer was diluted with water (4 vol) and the contents heated to 50-55° for 20-30 min. The layers were settled and then separated and the ethyl acetate layer was evaporated under reduced pressure to ~3 volumes. Ethyl Acetate (5 vol.) was added and again evaporated under reduced pressure to ~3 volumes. Cyclohexane (9 vol) was then added to the reactor and the contents were heated to reflux for 30 min then cooled to 0° C. The solids were filtered and rinsed with cyclohexane (2×100 mL). The solids were air dried overnight to obtain methyl 3-{[(2,6-difluorophenyl)sulfonyl]amino}-2-fluorobenzoate (94.1 g, 91%).

Step B: N-{3-[(2-chloro-4-pyrimidinyl)acetyl]-2-fluorophenyl}-2,6-difluorobenzenesulfonamide

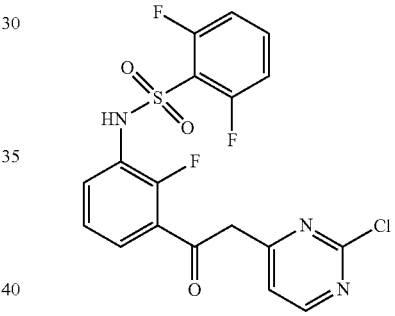

Methyl 3-{[(2,6-difluorophenyl)sulfonyl]amino}-2-fluorobenzoate (490 g, 1 equiv.), prepared generally in accordance with Step A, above, was dissolved in THF (2.45 L, 5 vols) and stirred and cooled to 0-3° C. 1M lithium bis(trimethylsilyl)amide in THF (5.25 L, 3.7 equiv.) solution was charged to the reaction mixture followed addition of 2-chloro-4-methylpyrimidine (238 g, 1.3 equiv.) in THF (2.45 L, 5 vols). The reaction was then stirred for 1 hr. The reaction was quenched with 4.5M HCl (3.92 L, 8 vols). The aqueous layer (bottom layer) was removed and discarded. The organic layer was concentrated under reduced pressure to ~2 L. IPAC (isopropyl acetate) (2.45 L) was added to the reaction mixture which was then concentrated to ~2 L. IPAC (0.5 L) and MTBE (2.45 L) was added and stirred overnight under N$_2$. The solids were filtered. The solids and mother filtrate added back together and stirred for several hours. The solids were filtered and washed with MTBE (~5 vol). The solids were placed in vacuum oven at 50° C. overnight. The solids were dried in vacuum oven at 30° C. over weekend to obtain N-{3-[(2-chloro-4-pyrimidinyl)acetyl]-2-fluorophenyl}-2,6-difluorobenzenesulfonamide (479 g, 72%).

Step C: N-{3-[5-(2-chloro-4-pyrimidinyl)-2-(1,1-dimethylethyl)-1,3-thiazol-4-yl]-2-fluorophenyl}-2,6-difluorobenzenesulfonamide

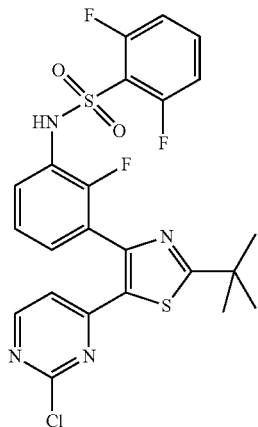 [SMILES: CC(C)(C)c1nc(-c2cccc(NS(=O)(=O)c3c(F)cccc3F)c2F)c(-c2ccnc(Cl)n2)s1]

To a reactor vessel was charged N-{3-[(2-chloro-4-pyrimidinypacetyl]-2-fluorophenyl}-2,6-difluorobenzenesulfonamide (30 g, 1 eq) followed by dichloromethane (300 mL). The reaction slurry was cooled to ~10° C. and N-bromosuccinimide ("NBS") (12.09 g, 1 eq) was added in 3 approximately equal portions, stirring for 10-15 minutes between each addition. After the final addition of NBS, the reaction mixture was warmed to ~20° C. and stirred for 45 min. Water (5 vol) was then added to the reaction vessel and the mixture was stirred and then the layers separated. Water (5 vol) was again added to the dichloromethane layer and the mixture was stirred and the layers separated. The dichloromethane layers were concentrated to ~120 mL. Ethyl acetate (7 vol) was added to the reaction mixture and concentrated to ~120 mL. Dimethylacetamide (270 mL) was then added to the reaction mixture and cooled to ~10° C. 2,2-Dimethylpropanethioamide (1.3 g, 0.5 eq) in 2 equal portions was added to the reactor contents with stirring for ~5 minutes between additions. The reaction was warmed to 20-25° C. After 45 min, the vessel contents were heated to 75° C. and held for 1.75 hours. The reaction mixture was then cooled to 5° C. and water (270 ml) was slowly charged keeping the temperature below 30° C. Ethyl acetate (4 vol) was then charged and the mixture was stirred and layers separated. Ethyl acetate (7 vol) was again charged to the aqueous layer and the contents were stirred and separated. Ethyl acetate (7 vol) was charged again to the aqueous layer and the contents were stirred and separated. The organic layers were combined and washed with water (4 vol) 4 times and stirred overnight at 20-25° C. The organic layers were then concentrated under heat and vacuum to 120 mL. The vessel contents were then heated to 50° C. and heptanes (120 mL) were added slowly. After addition of heptanes, the vessel contents were heated to reflux then cooled to 0° C. and held for ~2 hrs. The solids were filtered and rinsed with heptanes (2×2 vol). The solid product was then dried under vacuum at 30° C. to obtain N-{3-[5-(2-chloro-4-pyrimidinyl)-2-(1,1-dimethylethyl)-1,3-thiazol-4-yl]-2-fluorophenyl}-2,6-difluorobenzenesulfonamide (28.8 g, 80%).

Step D: N-{3-[5-(2-amino-4-pyrimidinyl)-2-(1,1-dimethylethyl)-1,3-thiazol-4-yl]-2-fluorophenyl}-2,6-difluorobenzenesulfonamide In 1 gal pressure reactor, a mixture of N-{3-[5-(2-chloro-4-pyrimidinyl)-2-(1,1-dimethylethyl)-1,3-thiazol-4-yl]-2-fluorophenyl}-2,6-difluorobenzenesulfonamide (120 g) prepared in accordance with Step C, above, and ammonium hydroxide (28-30%, 2.4 L, 20 vol) was heated in the sealed pressure reactor to 98-103° C. and stirred at this temperature for 2 hours. The reaction was cooled slowly to room temperature (20° C.) and stirred overnight. The solids were filtered and washed with minimum amount of the mother liquor and dried under vacuum. The solids were added to a mixture of EtOAc (15 vol)/water (2 vol) and heated to complete dissolution at 60-70° C. and the aqueous layer was removed and discarded. The EtOAC layer was charged with water (1 vol) and neutralized with aq. HCl to ~pH 5.4-5.5 and added water (1 vol). The aqueous layer was removed and discarded at 60-70° C. The organic layer was washed with water (1 vol) at 60-70° C. and the aqueous layer was removed and discarded. The organic layer was filtered at 60° C. and concentrated to 3 volumes. EtOAc (6 vol) was charged into the mixture and heated and stirred at 72° C. for 10 min, then cooled to 20° C. and stirred overnight. EtOAc was removed via vacuum distillation to concentrate the reaction mixture to ~3 volumes. The reaction mixture was maintained at ~65-70° C. for ~30 mins. Product crystals having the same crystal form as those prepared in Example 58b (and preparable by the procedure of Example 58b), above, in heptanes slurry were charged. Heptane (9 vol) was slowly added at 65-70° C. The slurry was stirred at 65-70° C. for 2-3 hours and then cooled slowly to 0-5° C. The product was filtered, washed with EtOAc/heptane (3/1 v/v, 4 vol) and dried at 45° C. under vacuum to obtain N-{3-[5-(2-amino-4-pyrimidinyl)-2-(1,1-dimethylethyl)-1,3-thiazol-4-yl]-2-fluorophenyl}-2,6-difluorobenzenesulfonamide (102.3 g, 88%).

Method 4: Compound B (mesylate salt)—N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate

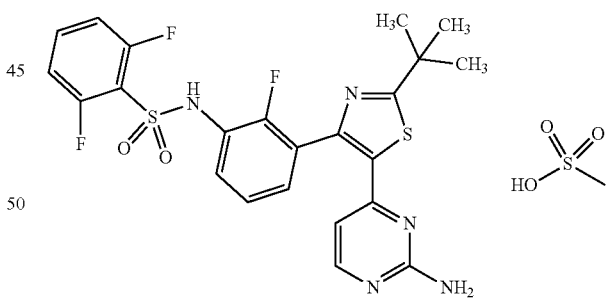

To a solution of N-{3-[5-(2-amino-4-pyrimidinyl)-2-(1,1-dimethylethyl)-1,3-thiazol-4-yl]-2-fluorophenyl}-2,6-difluorobenzenesulfonamide (204 mg, 0.393 mmol) in isopropanol (2 mL), methanesulfonic acid (0.131 mL, 0.393 mmol) was added and the solution was allowed to stir at room temperature for 3 hours. A white precipitate formed and the slurry was filtered and rinsed with diethyl ether to give the title product as a white crystalline solid (210 mg, 83% yield). $^1$H NMR (400 MHz, DMSO-d6) δ ppm 10.85 (s, 1H) 7.92-8.05 (m, 1H) 7.56-7.72 (m, 1H) 6.91-7.50 (m, 7H) 5.83-5.98 (m, 1H) 2.18-2.32 (m, 3H) 1.36 (s, 9H). MS (ESI): 520.0 [M+H]$^+$.

Method 5: Compound B (alternative mesylate salt embodiment)—N-{3-[5-(2-amino-4-pyrimidinyl)-2-(1,1-dimethylethyl)-1,3-thiazol-4-yl]-2-fluorophenyl}-2,6 difluorobenzenesulfonamide methanesulfonate N-{3-[5-(2-amino-4-pyrimidinyl)-2-(1,1-dimethylethyl)-1,3-thiazol-4-yl]-2-fluorophenyl}-2,6-difluorobenzenesulfonamide (as may be prepared according to example 58a) (2.37 g, 4.56 mmol) was combined with pre-filtered acetonitrile (5.25 vol, 12.4 mL). A pre-filtered solution of mesic acid (1.1 eq., 5.02 mmol, 0.48 g) in $H_2O$ (0.75 eq., 1.78 mL) was added at 20° C. The temperature of the resulting mixture was raised to 50-60° C. while maintaining a low agitation speed. Once the mixture temperature reached to 50-60° C., a seed slurry of N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate (1.0% w/w slurried in 0.2 vol of pre-filtered acetonitrile) was added, and the mixture was aged while agitating at a speed fast enough to keep solids from settling at 50-60° C. for 2 hr. The mixture was then cooled to 0-5° C. at 0.25° C./min and held at 0-5° C. for at 6 hr. The mixture was filtered and the wet cake was washed twice with pre-filtered acetonitrile. The first wash consisted of 14.2 ml (6 vol) pre-filtered acetonitrile and the second wash consisted of 9.5 ml (4 vol) pre-filtered acetonitrile. The wet solid was dried at 50° C. under vacuum, yielding 2.39 g (85.1% yield) of product.

Example 3: The In Vitro Effect on Proliferation of Combining the PIK3CA Inhibitor BYL719 (COMPOUND A) with the BRAF Inhibitor Dabrafenib (COMPOUND B) in BRAF Mutant Colorectal Cancer Cell Lines COMPOUNDS A and B were dissolved in 100% DMSO (Sigma, Catalog number D2650) at concentrations of 20 mM and stored at −20° C. until use. Compounds were arrayed in drug master plates (Greiner, Catalog number 788876) and serially diluted 3-fold (7 steps) at 2000× concentration.

Colorectal cancer cell lines used for this study were obtained, cultured and processed from commercial vendors ATCC, HSRRB, and CellBank Australia (Table 1). All cell line media were supplemented with 10% FBS (HyClone, Catalog number SH30071.03). Media for LIM2405 and LIM2551 was additionally supplemented with 0.6 μg/mL Insulin (SIGMA, Catalog number 19278), 1 μg/mL Hydrocortisone (SIGMA, Catalog number H0135), and 10 μM 1-Thioglycerol (SIGMA, Catalog number M6145).

Cell lines were cultured in 37° C. and 5% $CO_2$ incubator and expanded in T-75 flasks. In all cases cells were thawed from frozen stocks, expanded through ≥1 passage using 1:3 dilutions, counted and assessed for viability using a ViCell counter (Beckman-Coulter) prior to plating. To split and expand cell lines, cells were dislodged from flasks using 0.25% Trypsin-EDTA (GIBCO, Catalog number 25200). All cell lines were determined to be free of mycoplasma contamination as determined by a PCR detection methodology performed at Idexx Radil (Columbia, Mo., USA) and correctly identified by detection of a panel of SNPs.

To test the effect of the combination of COMPOUND A and COMPOUND B on cell proliferation cells were plated in black 384-well microplates with clear bottom (Matrix/Thermo Scientific, Catalog number 4332) in 50 μL media per well at cell densities between 500 and 1250 cells/well (Table 1) and allowed to incubate at 37 degrees, 5% $CO_2$ for 24 h. After 24 h one 384-well plate per cell line was prepared for cell counting by microscopy (see below) without receiving treatment (='baseline'). The other cell plates were treated by transferring 25 nL of the 2000× compound from drug master plates using an ATS acoustic liquid dispenser (ECD Biosystems) and resulting in a final 1× concentration. COMPOUND A was used over a final concentration range of 13 nM-10 μM, and COMPOUND B was used over a final concentration range of 1.4 nM-1 μM (7 1:3 dilution steps). For the combination of COMPOUND A with COMPOUND B the single agents were combined at a fixed ratio of 1:1 at each dilution resulting in 7 combination treatments. Additionally, negative controls (DMSO='vehicle') and positive controls (Staurosporine=killing cells, 7-point 1:2 dilution series for a dose range of 16 nm-1 μM) were transferred as treatment controls, and compounds with no efficacy in the cell lines tested were used in combinations with COMPOUND A and COMPOUND B as combination controls (combinations that do not exceed the efficacy of the more efficacious single agent='non-interacting' combinations). After compound addition 50 nL of 2 mM CellEvent Caspase-3/7 Green Detection Reagent (ThermoFisher, Catalog number C10423) were added to one of the three replicates using the HP D300 Digital Dispenser (Tecan). Caspase 3/7 induction was measured as a proxy for apoptosis induced by the treatments. Cells were treated for 72 h to 96 h depending on their doubling time (Table 1), and Caspase 3/7 activation was measured every 24 h by microscopy using an InCell Analyzer 2000 (GE Healthcare) equipped with a 4× objective and FITC excitation/emission filters. At the end of the treatment cells were prepared for cell counting by microscopy. Cells were fixed and permeabilised for 45 minutes in 4% PFA (Electron Microscopy Sciences, Catalog number 15714), 0.12% TX-100 (Electron Microscopy Sciences, Catalog number 22140) in PBS (Boston Bioproducts, Catalog number BM-220). After washing cells three times with

TABLE 1

Cell line information

| Cell line | Driver mutations | Source | Source Cat Num | Medium | Medium Vendor | Medium Cat Num | #Cells | Treatment [h] |
|---|---|---|---|---|---|---|---|---|
| RKO | BRAF, PIK3CA | ATCC | CRL-2577 | EMEM | ATCC | 30-2003 | 500 | 72 |
| LIM2551 | BRAF, PIK3CA | CellBank Australia | CBA-0170 | RPMI | ATCC | 30-2001 | 1000 | 72 |
| HT-29 | BRAF, PIK3CA | ATCC | HTB-38 | McCoy's 5A | ATCC | 30-2007 | 800 | 72 |
| LS411N | BRAF | ATCC | CRL-2159 | RPMI | ATCC | 30-2001 | 900 | 72 |
| COLO-205 | BRAF | ATCC | CCL-222 | RPMI | ATCC | 30-2001 | 800 | 72 |
| LIM2405 | BRAF | CellBank Australia | CBA-0165 | RPMI | ATCC | 30-2001 | 750 | 72 |
| OUMS-23 | BRAF | HSRRB | JCRB1022 | DMEM | ATCC | 30-2002 | 900 | 72 |

PBS their DNA was stained for 30 minutes with Hoechst 33342 (ThermoFisher, Catalog number H3570) at a final concentration of 4 μg/mL. Cells were washed three times with PBS and then plates were heat-sealed using a PlateLoc (Agilent Technologies) with aluminum seals (Agilent Technologies, Catalog number 06644-001) and stored at 4° C. until imaging. All cells per well/treatment were captured in a single image by fluorescence microscopy using an InCell Analyzer 2000 (GE Healthcare) equipped with a 4× objective and DAPI excitation/emission filters.

Images were analyzed after adapting previously described methods (Horn, Sandmann et al. 2011, Nat. Methods 8(4): 341-346) and using the Bioconductor package EBImage in R (Pau, Fuchs et al. 2010, Bioinformatics 26(7):979-981). Objects in both channels, DAPI (for Hoechst/DNA) and FITC (for Caspase 3/7), were segmented separately by adaptive thresholding and counted. A threshold for Caspase 3/7 positive objects was defined manually per cell line after comparing negative controls (DMSO) and positive controls (Staurosporine). By analyzing 17 additional object/nuclei features in the DNA channel (shape and intensity features) debris/fragmented nuclei were identified. To this end per cell line the distributions of the additional features between positive controls (Staurosporine) and negative controls (DMSO) were compared manually. Features that could differentiate between the conditions (e.g. a shift in the distribution of a feature measurement comparing DMSO with Staurosporine) where used to define the 'debris' population versus the population of 'viable' nuclei. The debris counts were subtracted from raw nuclei counts. The resulting nuclei number was used as measure of cell proliferation ('cell count').

The compound's effect on cell proliferation was calculated from the cell counts of the treatments relative to the cell counts of the negative control (DMSO), in FIG. 1 denoted as 'Normalized cell count' (='xnorm') on the y-axis. Synergistic combinations were identified using the highest single agent model (HSA) as null hypothesis (Berenbaum 1989). Excess over the HSA model predicts a functional connection between the inhibited targets (Lehar, Zimmermann et al. 2007, Lehar, Krueger et al. 2009). The model input were inhibition values per drug dose:

$$I = 1 - xnorm$$

I: inhibition xnorm: normalized cell count (median of three replicates)

At every dose point of the combination treatment the difference between the inhibition of the combination and the inhibition of the stronger of the two single agents was calculated (=model residuals). To favor combination effects at high inhibition the residuals were weighted with the observed inhibition at the same dose point. The overall combination score C of a drug combination is the sum of the weighted residuals over all concentrations:

$$C = \Sigma_{Conc}(I_{data} * (I_{data} - I_{model}))$$

$I_{data}$: measured inhibition $I_{model}$: inhibition according to HSA null hypothesis Robust combination z-scores ($z_C$) were calculated as the ratio of the treatments' combination scores C and the median absolute deviation (mad) of non-interacting combinations:

$$z_C = C / \mathrm{mad}(C_{zero})$$

$C_{zero}$: combination scores of non-interacting combinations $z_C$ is an indicator for the strength of the combination with:

$z_C \geq 3$: synergy $3 > z_C \geq 2$: weak synergy $z_C < 2$: no synergy

IC50 is the compound concentration that results in 50% of the cell counts relative to DMSO. IC50 calculations (see Table 2) were done using the DRC package in R (Ritz and Streibig January 2005, Journal of Statistical Software, "Bioassay analysis using R", 12:5:1-22) and fitting a four-parameter log-logistic function to the data.

Figure 2:
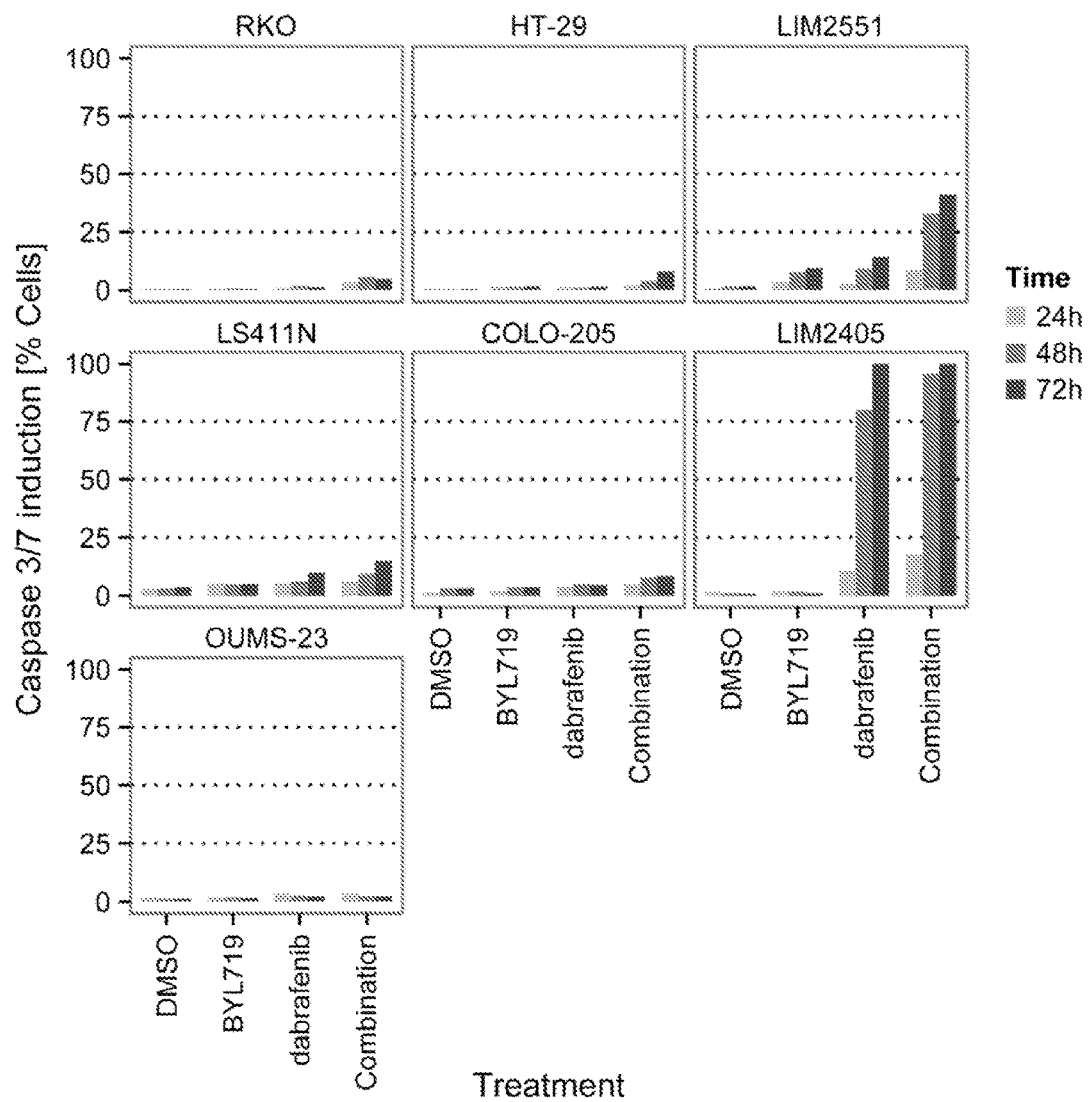
FIG. 2 shows maximum Caspase 3/7 induction for COMPOUND A (also referred to as BYL719) and COMPOUND B (also referred to as dabrafenib) and the combination of COMPOUND A and COMPOUND B in 7 BRAF mutant colorectal cancer cell lines and after 24 h, 48 h, and 72 h (different shades of grey). The x-axis indicates the treatment; the y-axis indicates the maximum Caspase 3/7 induction (% of cells) seen for each treatment.

The compound's effect on apoptosis was determined by calculating the percentage of cells with activated Caspase 3/7 per treatment and time point relative to the raw cell counts (before subtraction of debris) (y-axis in FIG. 2). Cell counts at time points that were not experimentally measured were obtained by regression analysis by fitting a linear model for log-transformed cell counts at day 0 and the end of the treatment (assuming exponential cell growth).

The efficacies of a PIK3CA inhibitor (BYL719, COMPOUND A) and a BRAF inhibitor (dabrafenib, COMPOUND B) were assessed individually and in combination in a total of 7 BRAF mutant colorectal cancer cell lines (3 also were mutant for PIK3CA) (Table 1). COMPOUND A as single agent specifically inhibited the growth of all cell lines with a mutation in PIK3CA with micromolar IC50 values (FIG. 1 and Table 2). Compound B as single agent strongly inhibited the growth of all but two cell lines (LS411N, OUMS-23) with nanomolar to sub-micromolar IC50 values (FIG. 1 and Table 2). The combination treatment caused synergistic inhibition (according to the HSA model) in all but one line (OUMS-23) with different strengths (Table 2). Combinations generally had stronger effects in cell lines with a PIK3CA mutation. The combination also induced apoptosis (assessed by measuring Caspase 3/7 induction) to different degrees in the cell models tested (FIG. 2), with the strongest inductions seen in LS411N and LIM2405. Combined inhibition of PIK3CA and BRAF in BRAF mutant colorectal cancer may provide an effective therapeutic modality capable of improving responses compared to each of the single agents and lead to more durable responses in the clinic.

TABLE 2

Single agent IC50 values for each compound and synergy z-score measurements for the combination of COMPOUND A and COMPOUND B.

| Cell | IC50 COMPOUND A | IC50 COMPOUND B | Synergy z-score ($z_C$) |
|---|---|---|---|
| RXO | 2.6 | 0.191 | 18.8 |
| HT-29 | 1.9 | 0.012 | 13.4 |
| LIM2551 | 1.4 | 0.023 | 12.5 |
| LS411N | >10 | >1 | 9.6 |
| COLO-205 | >10 | 0.01 | 8.3 |
| LIM2405 | >10 | 0.007 | 6.3 |
| OUMS-23 | >10 | >1 | 1.5 |

The invention claimed is:

1. A method for treating a colorectal cancer in a subject in need thereof comprising administering to the subject a therapeutically effective amount of a pharmaceutical combination comprising:

(a) a compound having the structure of Formula (I)

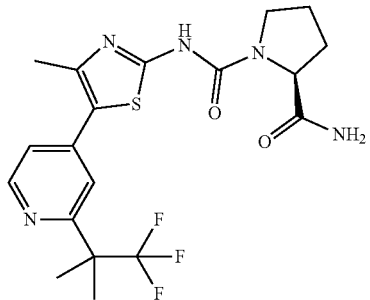

(I)

or a pharmaceutically acceptable salt thereof, and (b) a compound having the structure of Formula (II)

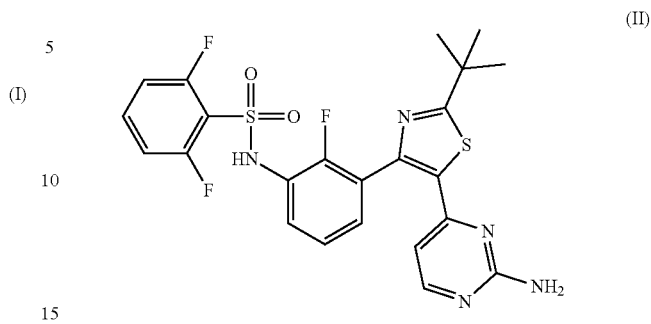

(II)

or a pharmaceutically acceptable salt thereof.

2. The method according to claim 1, wherein the cancer is characterized by one or more of B-RAF mutation, B-RAF V600E mutation, PIK3CA mutation, and PIK3CA overexpression.

3. The method according to claim 1, wherein the cancer is resistant or refractory to treatment with a B-RAF inhibitor.

* * * * *